US009625389B2

(12) United States Patent
Shiozawa et al.

(10) Patent No.: US 9,625,389 B2
(45) Date of Patent: Apr. 18, 2017

(54) LIGHT MEASURING DEVICE AND LIGHT MEASURING METHOD

(71) Applicant: Hitachi High-Technologies Corporation, Minato-ku, Tokyo (JP)

(72) Inventors: Manabu Shiozawa, Tokyo (JP); Koichi Watanabe, Tokyo (JP); Masataka Shirai, Tokyo (JP); Kentaro Osawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/036,241

(22) PCT Filed: Sep. 22, 2014

(86) PCT No.: PCT/JP2014/075038
§ 371 (c)(1),
(2) Date: May 12, 2016

(87) PCT Pub. No.: WO2015/079786
PCT Pub. Date: Jun. 4, 2015

(65) Prior Publication Data
US 2016/0299080 A1   Oct. 13, 2016

(30) Foreign Application Priority Data

Nov. 27, 2013  (JP) ................. 2013-245173

(51) Int. Cl.
*G01J 3/44* (2006.01)
*G01N 21/65* (2006.01)

(52) U.S. Cl.
CPC ....... *G01N 21/65* (2013.01); *G01N 2021/653* (2013.01); *G01N 2201/0638* (2013.01); *G01N 2201/06113* (2013.01)

(58) Field of Classification Search
CPC ............ G01N 21/65; G01N 2021/653; G01N 2201/06113; G01N 2201/0638
(Continued)

(56) References Cited

U.S. PATENT DOCUMENTS

| 2011/0282166 A1* | 11/2011 | Chen | ................... A61B 5/0084 600/306 |
| 2012/0092662 A1 | 4/2012 | Langbein et al. | |

(Continued)

FOREIGN PATENT DOCUMENTS

| JP | 2008-253493 A | 10/2008 |
| JP | 2009-222531 A | 10/2009 |

(Continued)

OTHER PUBLICATIONS

International Search Report (PCT/ISA/210) issued in PCT Application No. PCT/JP2014/075038 dated Dec. 16, 2014 with English translation (Four (4) pages).

(Continued)

*Primary Examiner* — Hina F Ayub
(74) *Attorney, Agent, or Firm* — Crowell & Moring LLP

(57) ABSTRACT

To measure a surface state, reflective CARS is suitable in terms of the signal intensity. However, with the reflective CARS, it has been difficult to identify the surface position because the shape information is not acquired. Thus, a reflective CARS microscope is combined with a high-resolution phase sensor. The surface position is identified with the phase sensor, and reflected CARS generated from the surface is detected, so that composition analysis is performed.

9 Claims, 15 Drawing Sheets

(58) Field of Classification Search
USPC .......................................................... 356/301
See application file for complete search history.

(56) References Cited

U.S. PATENT DOCUMENTS

| | | | |
|---|---|---|---|
| 2012/0281229 A1* | 11/2012 | Montgomery | A61B 5/0084 |
| | | | 356/477 |
| 2012/0300217 A1 | 11/2012 | Yuasa | |
| 2014/0253919 A1 | 9/2014 | Yui | |
| 2015/0005641 A1 | 1/2015 | Toida | |
| 2015/0276483 A1 | 10/2015 | Mikami | |

FOREIGN PATENT DOCUMENTS

| | | |
|---|---|---|
| JP | 2011-218155 A | 11/2011 |
| JP | 2012-521001 A | 9/2012 |
| JP | 2013-174530 A | 9/2013 |
| JP | 2013-182653 A | 9/2013 |
| WO | WO 2013/047698 A1 | 4/2013 |
| WO | WO 2013/129412 A1 | 9/2013 |
| WO | WO 2014/061147 A1 | 4/2014 |

OTHER PUBLICATIONS

Japanese-language Written Opinion (PCT/ISA/237) issued in PCT Application No. PCT/JP2014/075038 dated Dec. 16, 2014 (Four (4) pages).

Cheng, J., et al., "Coherent Anti-Stokes Raman Scattering Microscopy: Instrumentation, Theory, and Applications", J. Phys. Chem. B, 2004, vol. 108, No. 3, pp. 827-840 (Fourteen (14) pages).

* cited by examiner

Fig. 8

| Scheme | Phase Sensor of Present Invention | Time Domain OCT | Fourier Domain OCT | |
|---|---|---|---|---|
| | | | Wavelength-Scanning OCT | Spectral Domain OCT |
| Light Source | High-Coherence Light Source | Low-Coherence Light Source | Wavelength-Scanning Light Source | Low-Coherence Light Source |
| Scanning Method in Depth Direction | Objective Lens Scanning | Reference Beam Mirror Scanning | Wavelength Scanning | Spectroscopy |
| Depth Resolution | ≦3 µm (Intensity) ≦50 nm (Phase) | 10 µm | 5 µm | 5 µm |

Fig. 9

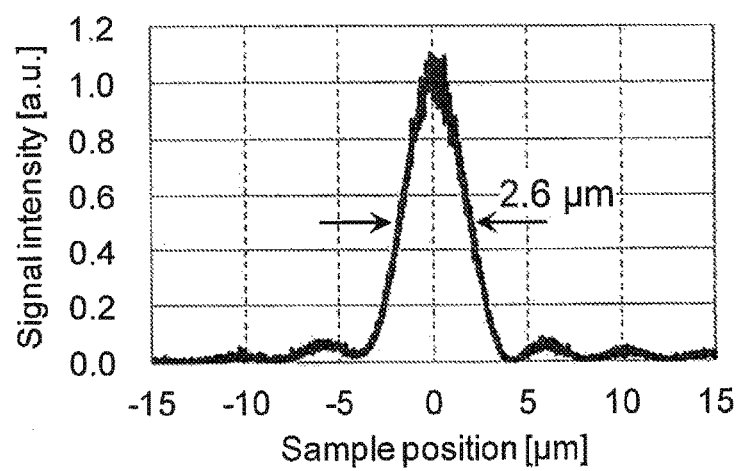

LIGHT MEASURING DEVICE AND LIGHT MEASURING METHOD

TECHNICAL FIELD

The present invention relates to an optical measuring device and an optical measuring method for acquiring the composition of and the shape information on a measurement target using light beams.

BACKGROUND ART

In recent years, optical measurement techniques, such as a CARS (Coherent Anti-Stokes Raman Scattering) microscope and OCT (Optical Coherence Tomography), have been drawing attention and are expected to be applied to the field of biology or medical care, in particular, due to its non-invasiveness to measurement targets. Conventionally, for analyzing a cell, a method of dying and invading the cell using a reagent and observing the cell with a microscope or the like has been commonly conducted. However, if the aforementioned optical measurement techniques are used, it becomes possible to continuously analyze an identical cell or directly use an inspected cell for medical treatment, for example.

CARS is based on a nonlinear optical phenomenon that when two light beams with different wavelengths are allowed to become incident on an object, a CARS beam is obtained that has a wavelength corresponding to the vibration of molecules forming the object, and is described in Patent Literature 1, for example. A plurality of different methods, such as transmissive CARS and reflective CARS, have been proposed regarding the direction of detecting a CARS beam with respect to the incident direction of a pump beam and a Stokes beam. Non Patent Literature 1 describes, as a feature of reflective CARS, that the dependence on the sample size of the intensity of a CARS beam is large due to the discontinuity of a nonlinear constant, and the intensity rapidly decreases with an increase in the size. Non Patent Literature 1 also describes that, due to such feature, reflective CARS is advantageous for measuring a microscale sample in a medium, such as a culture solution, and that the intensity increases at an interface between two different media, and shows the experimental data in FIG. 14 in which a peak of a reflective CARS signal is obtained at an interface between oil and glass.

Meanwhile, OCT is a method of obtaining shape information, which reflects a change in the refractive index, using interference between a reflected beam from an object and a reference beam that has not irradiated the object, and is described in Patent Literature 2, for example. While a CARS microscope can obtain molecular information on a measurement target, OCT can obtain shape information. Thus, the two techniques are in a mutually complementary relationship. Patent Literature 3 discloses a multi-modal measurement device that combines CARS and OCT, and provides "a measurement device and a measurement method capable of simultaneously measuring structural information and molecular information about a subject."

CITATION LIST

Patent Literature

Patent Literature 1: JP 2009-222531 A
Patent Literature 2: JP 2011-218155 A
Patent Literature 3: JP 2013-174530 A

Non Patent Literature

Non Patent Literature 1: Ji-Xin Cheng and X. Sunney Xie, "Coherent Anti-Stokes Raman Scattering Microscopy: Instrumentation, Theory, and Applications," J. Phys. Chem. B, Vol. 108, 827-840 (2004)

SUMMARY OF INVENTION

Technical Problem

Depending on measurement targets or objectives, there may be cases where information on an interface between a measurement target and the outside of the measurement target should be acquired rather than information on the inside of the measurement target. For example, in analyzing cells, it is important to acquire information on receptors that appear on the surface of a cell membrane as well as molecules that bind to the receptors. Accordingly, cancerization of cells and the like can be analyzed. For measuring a surface state, the aforementioned reflective CARS is preferable in terms of the signal intensity. However, with the reflective CARS, it is difficult to identify the surface position because the shape information is not acquired. A cell membrane has a thickness of less than or equal to 10 nm, and the position adjustment accuracy on the order of nanometers is thus required.

According to the technique of Patent Literature 3 above, the pulse of a pump beam is stretched so that the pulse width of a Stokes beam becomes shorter than the that of the pump beam, and an anti-Stokes beam is used as a CARS beam, while the Stokes beam is used as an OCT measurement beam, so that CARS and OCT are combined while avoiding a mismatch between the optical pulses that would otherwise occur when CARS and OCT are combined. Thus, as the configuration of Patent Literature 3 is not intended to detect the surface position, it is impossible to perform adjustment with such precision.

Solution to Problem

An optical measuring device of the present invention includes a sample stage that holds a sample; a pump beam generation unit configured to generate a pump beam; a Stokes beam generation unit configured to generate a Stokes beam, the Stokes beam having a wavelength longer than that of the pump beam; a reference beam splitting unit configured to split off a reference beam from the pump beam or the Stokes beam; a combining unit configured to coaxially combine the pump beam with the Stokes beam; an objective lens configured to focus the combined beam of the pump beam and the Stokes beam onto the sample held on the sample stage; a position control unit configured to control a relative position between the objective lens and the sample held on the sample stage; a phase sensor configured to identify a surface position of the sample by causing a reflected beam from the sample that has passed through the objective lens and the reference beam to interfere with each other and detecting an intensity of the reflected beam or a phase of the reflected beam with respect to the reference beam; and a detector configured to detect a reflected CARS beam generated from the sample.

The phase sensor is configured to detect the surface position of the sample with an accuracy of less than or equal to 3 micrometers in an optical-axis direction.

In addition, a numerical aperture of the objective lens is greater than or equal to 0.4.

The phase sensor includes an interferometer configured to generate at least three interference beams having a phase difference with respect to each other, and is configured to output a signal proportional to the intensity of the reflected beam, and a signal representing the phase of the reflected beam with respect to the reference beam.

As an example, the pump beam generation unit includes a short-pulse laser source, and the Stokes beam generation unit includes a wavelength conversion unit configured to generate the Stokes beam by converting a wavelength of a light beam emitted from the short-pulse laser source.

As another example, the pump beam generation unit includes a first short-pulse laser source, the Stokes beam generation unit includes a second short-pulse laser source, and the optical measuring device further includes a synchronizing unit configured to synchronously drive the first short-pulse laser source and the second short-pulse laser source.

As still another example, the reference beam is split off from the pump beam, and the phase sensor is configured to output a signal proportional to an intensity of the pump beam reflected from the sample, and a signal representing a phase of the pump beam reflected from the sample with respect to the reference beam.

An optical measuring method of the present invention includes focusing a pump beam with an objective lens and irradiating a sample with the focused pump beam; detecting a surface position of the sample with a phase sensor using an interference beam of the pump beam reflected from the sample and the pump beam that has not irradiated the sample; adjusting a focus position of the objective lens to the detected surface position of the sample; irradiating the sample with a combined beam of a Stokes beam and the pump beam via the objective lens, the Stokes beam having a wavelength longer than that of the pump beam; and detecting a reflected CARS beam generated from the sample.

Herein, the phase sensor is configured to generate at least three interference beams having a phase difference with respect to each other, detect the surface position of the sample using an intensity signal that is proportional to an intensity of the reflected beam, and determine a phase of the reflected beam with respect to the reference beam upon detection of the surface position of the sample.

Further, the method includes controlling a relative position between the objective lens and the sample in an optical-axis direction so that the determined phase is maintained.

Advantageous Effects of Invention

According to the present invention, it is possible to detect the surface position of a measurement target with high accuracy and thus acquire molecular information on the surface.

Other problems, configurations, and advantageous effects will become apparent from the following description of embodiments.

BRIEF DESCRIPTION OF DRAWINGS

FIG. 8 is a diagram in which the phase sensor in accordance with the present invention is compared with the conventional OCT.

FIG. 9 is a diagram showing the resolution of the phase sensor in accordance with the present invention.

DESCRIPTION OF EMBODIMENTS

First, Raman scattering and CARS will be briefly described.

Figure 15:
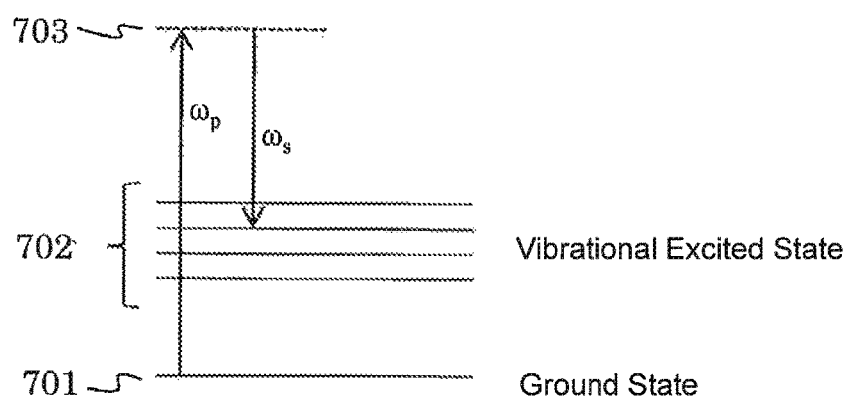
FIG. 15 is an energy level diagram of the Stokes scattering in the usual Raman scattering.

FIG. 15 shows a process in which Raman scattering occurs, using an energy level diagram. Raman scattering includes Stokes scattering and anti-Stokes scattering. FIG. 15 shows only the Stokes scattering. Reference numeral 701 denotes the molecular ground state, and reference numeral 702 denotes the vibrational excited state. When a molecule is irradiated with a pump beam with a frequency $\omega_P$, a beam with a frequency $\omega_S$ is scattered after an intermediate state 703 is once reached. At this time, the molecule falls back to one of the levels of the vibrational excited state 702. The scattered beam with the frequency $\omega_S$ is a Stokes beam with a frequency lower than that of the pump beam. The molecular vibrational excited state has a plurality of levels, and the vibrational excited state differs depending on the types of molecules. Further, as the probability of transition from the level of the intermediate state to the level of the vibrational excited state differs from molecule to molecule, a spectrum that is unique to the molecule is formed. The Raman shift frequency $\Omega$ is represented by $\Omega=\omega_P-\omega_S$, and has a positive value in the case of Stokes scattering. In the case of an anti-Stokes beam, the initial molecular state is the vibrational excited state, and the molecular state falls back to the ground state after an intermediate level is once reached. In such a case, if the frequency of the anti-Stokes beam is represented by $\omega_{AS}$, $\omega_P < \omega_{AS}$. Thus, the frequency of the anti-Stokes Raman scattering beam is higher than that of the pump beam.

Measurement of the aforementioned Raman scattering takes a long time as the intensity of the obtained scattered light is weak. As a method that can obtain intense scattered light, there is known spectroscopy using CARS (Coherent Anti-Stokes Raman Scattering) that is nonlinear Raman scattering. Using such a method can also obtain a Raman spectrum and know the molecular vibrational state. To generate CARS, pulsed laser with a high peak power is used. CARS is generated from such a pulsed laser beam due to the nonlinear effect, and the intensity of the CARS can be orders of magnitude higher than that of Raman scattering as the peak power is higher. Accordingly, it is possible to obtain a signal with a high signal-noise ratio and significantly reduce the measurement time.

CARS is based on the third-order polarization. In order to generate CARS, a pump beam, a Stokes beam, and a probe beam are needed. Typically, the pump beam is substituted for the probe beam in order to reduce the number of light sources. In that case, the induced third-order polarization is represented as follows.

$$P_{AS}^{(3)}(\omega_{AS}) = |\chi_r^{(3)}(\omega_{AS}) + \chi_{nr}^{(3)}|E_P^2(\omega_P)E_S^*(\omega_S)$$

Herein, $\chi_r^{(3)}(\omega_{AS})$ is a resonant term of a vibration of a molecule with the third-order electric susceptibility, and $\chi_{nr}^{(3)}$, which has no frequency dependence, is a nonresonant term. In addition, the electric fields of the pump beam and the probe beam are represented by $E_P$, and the electric field of the Stokes beam is represented by $E_S$. In the above Formula, the asterisk that appears in $E_S$ represents the complex conjugate. The intensity of a CARS beam is represented as follows.

$$I_{CARS}(\omega_{AS}) \propto |P_{AS}^{(3)}(\omega_{AS})|^2$$

Figure 16:
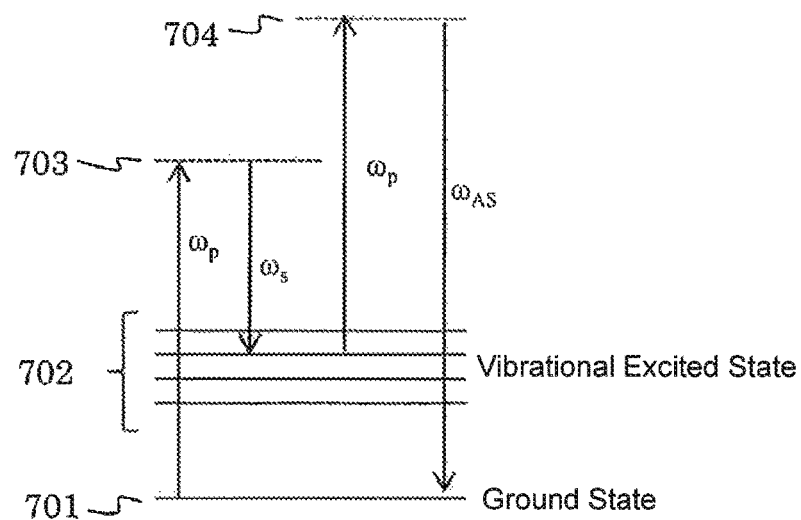
FIG. 16 is an energy level diagram of CARS.

A mechanism by which a CARS beam is generated will be described using a molecular energy level diagram shown in FIG. 16. FIG. 16 shows a process of the resonant term. As in FIG. 15, reference numeral 701 denotes the molecular ground state, and reference numeral 702 denotes the vibrational excited state. A molecule is simultaneously irradiated with a pump beam with a frequency $\omega_P$ and a Stokes beam with a frequency $\omega_S$. At this time, the molecule is excited to a level of the vibrational excited state 702 after an intermediate state 703 is once reached. When the molecule in the excited state is irradiated with a probe beam with a frequency $\omega_P$, the molecule falls back to the ground state while generating a CARS beam with a frequency $\omega_{AS}$ after an intermediate state 704 is once reached. The frequency of the CARS beam at this time is represented by $\omega_{AS} = 2 \cdot \omega_P - \omega_S$.

Figure 17:
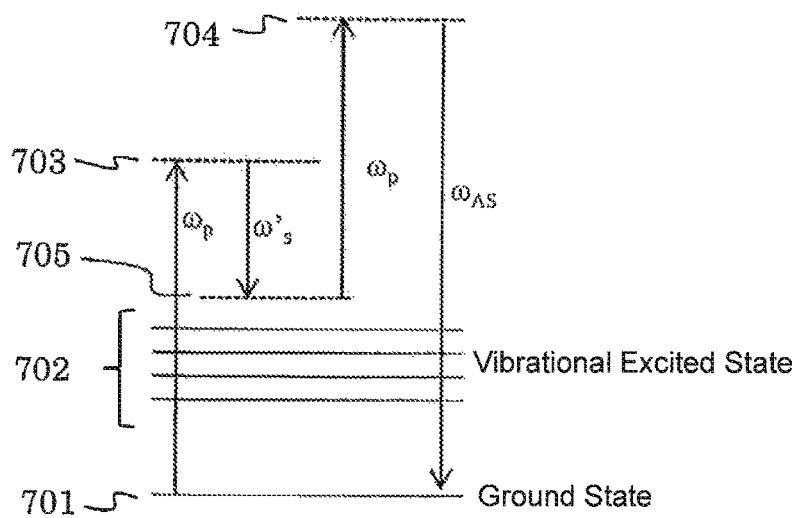
FIG. 17 is an energy level diagram illustrating an example of a non-resonant beam in CARS.
Figure 18:
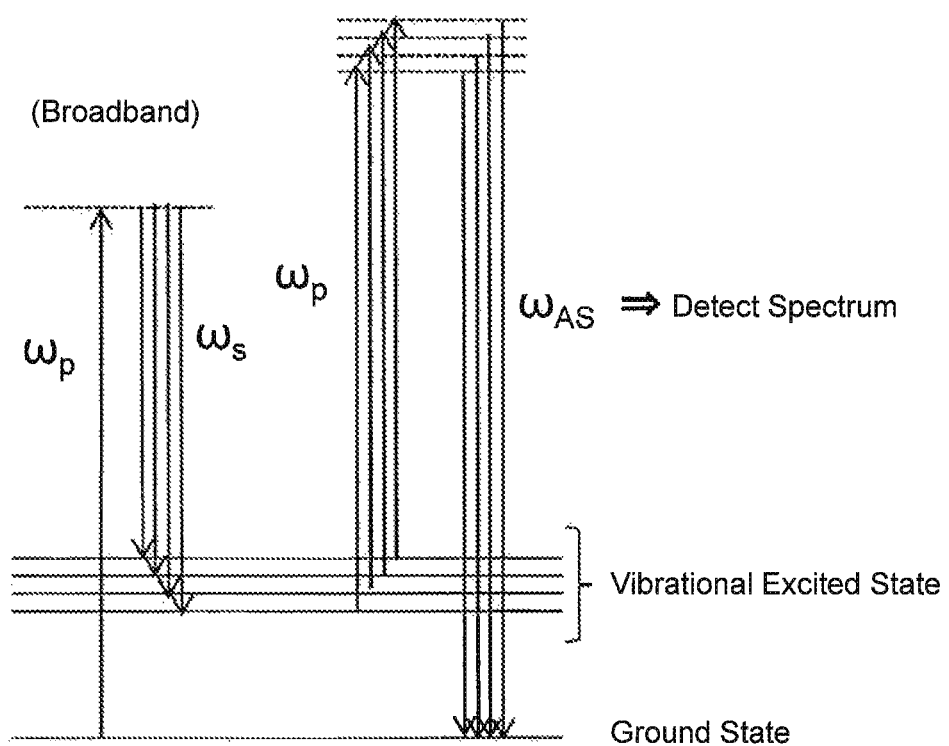
FIG. 18 is an energy level diagram of CARS when a broadband laser beam is used as a Stokes beam.

FIG. 17 shows a process related to the nonresonant term $\chi_{nr}^{(3)}$ of the third-order polarization. This is a process in which the frequency of the Stokes beam is not determined by the vibrational excited state but by an intermediate state 705. The intermediate state 705 in which electrons and the like are involved is excited when a molecule is simultaneously irradiated with a pump beam with a frequency $\omega_P$ and a Stokes beam with a frequency $\omega'_S$. When the molecule is further irradiated with a probe beam with a frequency $\omega_P$, a nonresonant CARS beam with a frequency $\omega_{AS}$ is generated after an intermediate state 704 is once reached. If a broadband laser beam is used as a Stokes beam, it is possible to acquire a spectrum corresponding to a plurality of excited states as shown in FIG. 18. If a spectrometer is used for a detector, multi-color CARS can be detected.

Hereinafter, embodiments of the present invention will be described with reference to the drawings.

[Embodiment 1]

Figure 1:
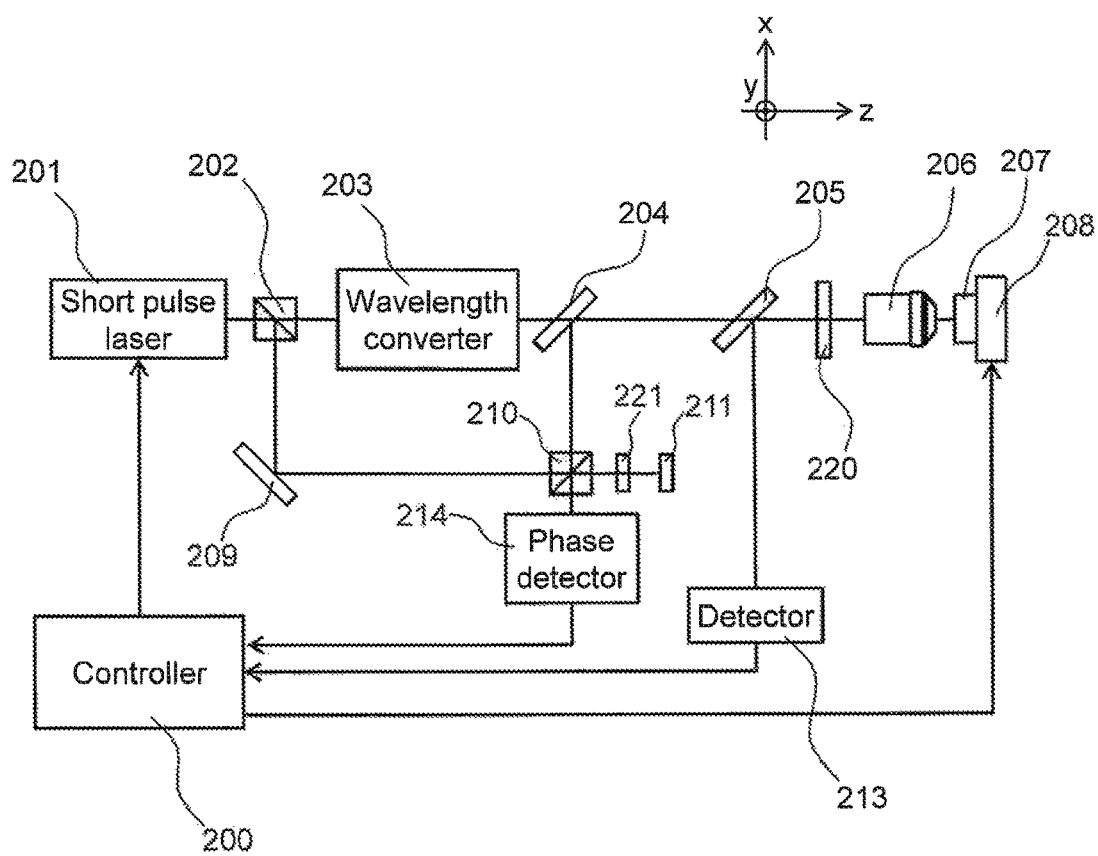
FIG. 1 is a schematic diagram showing the basic embodiment of an optical measuring device in accordance with the present invention.
Figure 2:
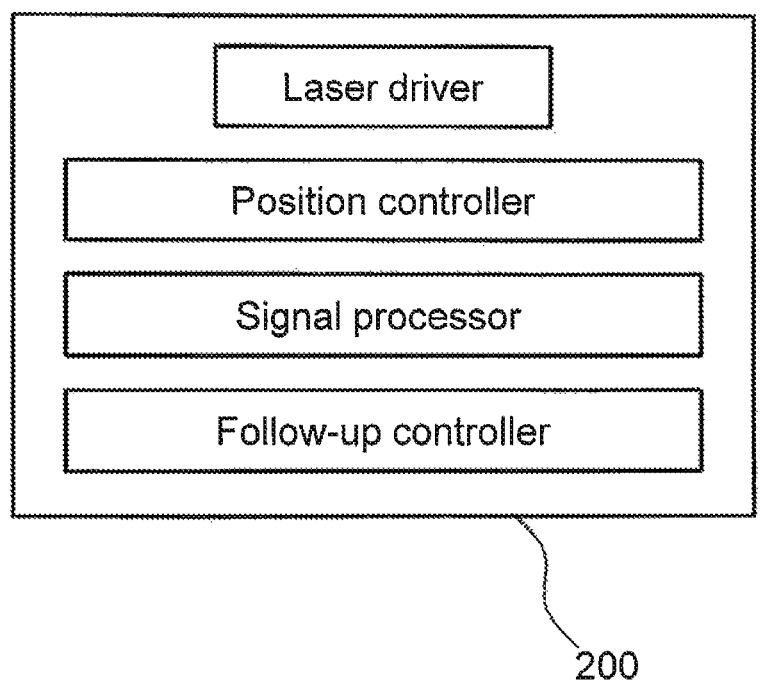
FIG. 2 is a diagram showing a configuration example of a controller of the device in accordance with the present invention.

FIG. 1 is a schematic diagram showing the basic embodiment of an optical measuring device in accordance with the present invention. This device includes a reflective CARS microscope, a phase sensor, and a controller 200 that controls the entire device. The controller 200 includes, as shown in FIG. 2, a laser driver that controls a short-pulse laser source, a position controller that controls the position of a sample stage as well as each optical element, such as an objective lens or a mirror, a signal processor that performs signal processing on signals obtained from the CARS microscope and the phase sensor, generates an image, and detects the surface position, and a follow-up controller that causes a focus position of a laser beam to follow the detected surface position. It should be noted that the optical measuring device need not include all of the configurations described herein, and the configurations may be determined based on the functions and accuracy that are necessary.

(Configuration of the CARS Microscope)

Next, the configuration of the CARS microscope will be described. A short-pulse laser source 201 emits a short-pulse laser beam based on an instruction from the controller 200. The short-pulse laser source 201 is, for example, a titanium-sapphire laser or a fiber laser, and has a pulse width of less than or equal to nanoseconds. The peak power is desirably greater than or equal to the order of kilowatts with which a nonlinear optical effect can be induced. The wavelength may be selected from among the wavelengths to be absorbed by a measurement target and the corresponding wavelengths of the optical components used. For example, the wavelength is 800 nm or 1064 nm.

A laser beam is split into two light beams that are a Stokes beam and a pump beam by a beam splitter 202. The laser beam split as the Stokes beam becomes incident on a wavelength converter 203, and is converted into a beam with a wavelength longer than that of the pump beam. Examples of the wavelength converter include a photonic crystal fiber and an OPO (Optical Parametric Oscillator). A photonic crystal fiber is an optical fiber that has a honeycomb cladding formed around a core, and strongly confines the incident light beam to the inside of the core. When a short-pulse laser beam is allowed to become incident on such a photonic crystal fiber, a nonlinear optical phenomenon, such as self-phase modulation or four-wave mixing, is induced, and a broadband light beam with a broad spectrum is generated. Among the components of such light beam, components with a wavelength longer than that of the pump beam may be used for the Stokes beam. Meanwhile, OPO has a function of converting the wavelength of the incident light beam by optical parametric generation, and sweeps the wavelength of the output light beam by changing the angle of a nonlinear medium provided in the device, for example.

The wavelength-converted Stokes beam passes through a dichroic mirror 204, which reflects only the pump beam wavelength, and through a long-pass filter 205, and then becomes incident on a λ/4 plate 220. The λ/4 plate 220 has an optical-axis direction set at about 22.5 degrees with respect to the horizontal direction, and converts a transmitted light beam from a linearly polarized state into a circularly polarized state. The Stokes beam that has passed through the λ/4 plate 220 is focused onto a cell sample 207 by an objective lens 206. The numerical aperture of the objective lens 206 should be selected in accordance with the spatial resolution that is necessary. For example, using an objective lens with a numerical aperture of greater than or equal to 0.4 can surely obtain the spatial resolution that is necessary. Meanwhile, in order to secure the working distance, the numerical aperture is preferably less than or equal to 1.33. The focus position on the sample 207 is controlled on a sample stage 208, which uses a piezo element, a stepping motor, and the like, by the controller 200.

Meanwhile, the laser beam split as the pump beam by the beam splitter 202 is reflected by a mirror 209, and the s-polarized components are reflected by a polarization beam splitter 210 and a dichroic mirror 204, and then are coaxially combined with the Stokes beam. It should be noted that the p-polarized components pass through the polarization beam splitter 210, and are split as the reference beam of the phase sensor. The pump beam reflected by the dichroic mirror 204 passes through the long-pass filter 205 and is circularly polarized by the λ/4 plate 220, and then is focused onto the sample 207 by the objective lens 206.

When the Stokes beam and the pump beam are focused onto the same position of the sample 207, a molecular vibration that resonates with the frequency difference between the two beams is induced, thus generating a CARS beam. At this time, if a broadband light beam obtained with a photonic crystal fiber is used as the Stokes beam, a plurality of molecular vibrations are induced concurrently, whereby a CARS beam with a broad spectrum is obtained. Meanwhile, if a wavelength-converted light beam obtained with an OPO is used, the resulting CARS beam also has a single wavelength. However, sweeping the wavelength with the OPO can also obtain a similar spectrum to that when a broadband light beam is used.

The generated CARS beam is collimated by the objective lens 206, and then passes through the λ/4 plate 220 again, so that the beam is converted from the circularly polarized state into a p-polarized state. As the CARS beam has a wavelength shorter than those of the pump beam and the Stokes beam, the CARS beam is reflected by the long-pass filter and then becomes incident on a photodetector 213. Examples of the photodetector 213 include a spectrometer. However, if an OPO is used as the wavelength converter 203, a PD (Photo Diode) may be used. The spectral peak position of the CARS beam is made to coincide with the resonant frequency of each molecular vibration by the controller 200, whereby the molecular information on the sample 207 can be obtained. When such a process is performed while the focus position of the laser beam is changed, it is possible to obtain a spectral image corresponding to a molecular distribution of the sample 207. For example, when a distribution of the C-H expansion and contraction is obtained, the intensity at about 2850 cm$^{-1}$ may be mapped to the sample position.

(Configuration of the Phase Sensor)

Next, the configuration of the phase sensor will be described. The phase sensor includes the polarization beam splitter 210, a λ/4 plate 221, a mirror 211, and a phase detector 214, and detects the surface of the sample 207 using a pump beam. A pump beam that has been focused onto the sample 207 is reflected at an interface between two media with different refractive indices, such as the surface of a cell membrane. The reflected pump beam is collimated by the objective lens 206 as a signal beam holding the phase information at the interface, and passes through the λ/4 plate 220 again, so that the beam is converted from the circularly polarized state into a p-polarized state. The signal beam that has passed through the λ/4 plate 220 passes through the long-pass filter 205 and is reflected by the dichroic mirror 204, and then becomes incident on the polarization beam splitter 210. The signal beam, which is a p-polarized beam, passes through the polarization beam splitter 210, and becomes incident on the phase detector 214. Meanwhile, the reference beam passes through the λ/4 plate 221, and is converted from the p-polarized state into a circularly polarized state, and then becomes incident on and is reflected by the mirror 211 whose position is fixed, and passes through the λ/4 plate 221 again, so that the beam is converted from the circularly polarized state into a s-polarized state. The s-polarized reference beam is reflected by the polarization beam splitter 210 and is combined with the signal beam, and then becomes incident on the phase detector 214. The phase detector 214 detects the intensity of the signal beam and the phase of the signal beam with respect to the reference beam. It should be noted that a configuration example of the phase detector 214 will be described below.

Based on the obtained intensity and phase information, the controller 200 acquires the position of and the shape information on the surface of the cell membrane. The controller 200 also controls the position of the sample as appropriate such that the focus position of the laser beam follows the surface of the cell membrane. In such a case, the sample stage 208 may be feedback-controlled controlled such that a phase detected by the phase sensor is within a predetermined range.

Figure 3:
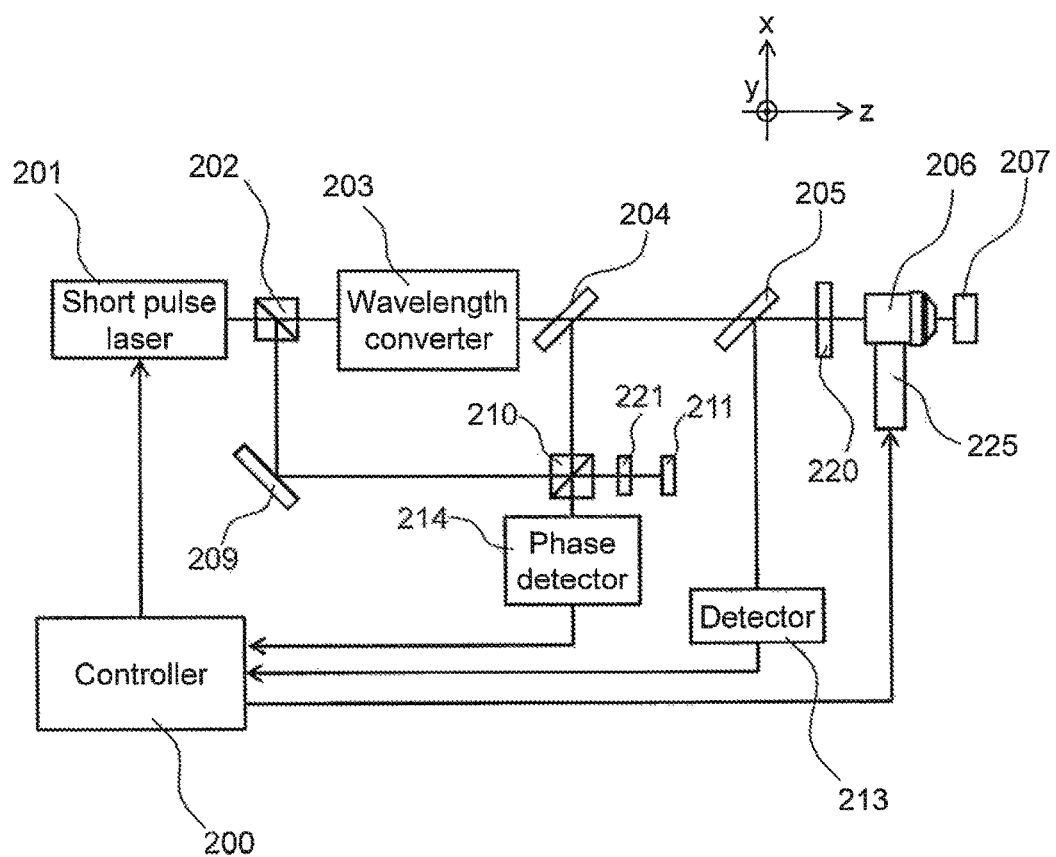
FIG. 3 is a schematic diagram when the position of an objective lens is controlled.
Figure 4:
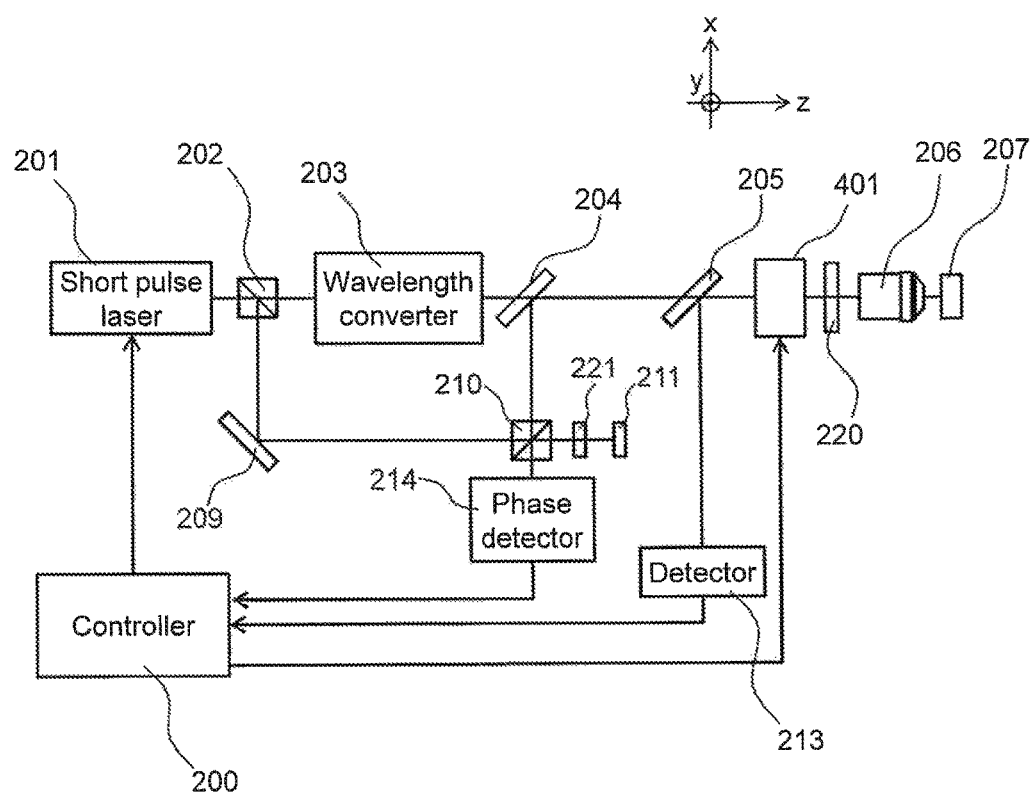
FIG. 4 is a schematic diagram when optical path changing means, such as a galvanometer mirror or a space phase modulator, is used.

Although an example is shown in which the sample is moved to control the focus position of the laser beam herein, it is also possible to move the objective lens 206 using an actuator 225 and the like while fixing the sample as shown in FIG. 3. In addition, it is also possible to insert optical path changing means 401, such as a galvanometer mirror or a space phase modulator, as shown in FIG. 4 so as to change the focus position of the laser beam. In such a case, the optical path lengths of the signal beam and the reference beam change with a movement of the spot in the z direction. Thus, not a phase but intensity information may be used. In addition, in order to cause the two beams to interfere with each other, it is necessary to use as the short-pulse laser source 201 a light source with a coherence length that is greater than or equal to a distance obtained by multiplying the movement amount of the spot in the z direction by the refractive index of the sample. As the coherence length increases with an increase in the laser pulse width, a laser of several picoseconds or hundreds of picoseconds may be used. Meanwhile, when the position of the sample is changed as shown in FIG. 1, it is acceptable as long as a coherent length is secured that corresponds to the amount of change in the spot position in the z direction generated by the difference in refractive index between the air and the sample.

Figure 5:
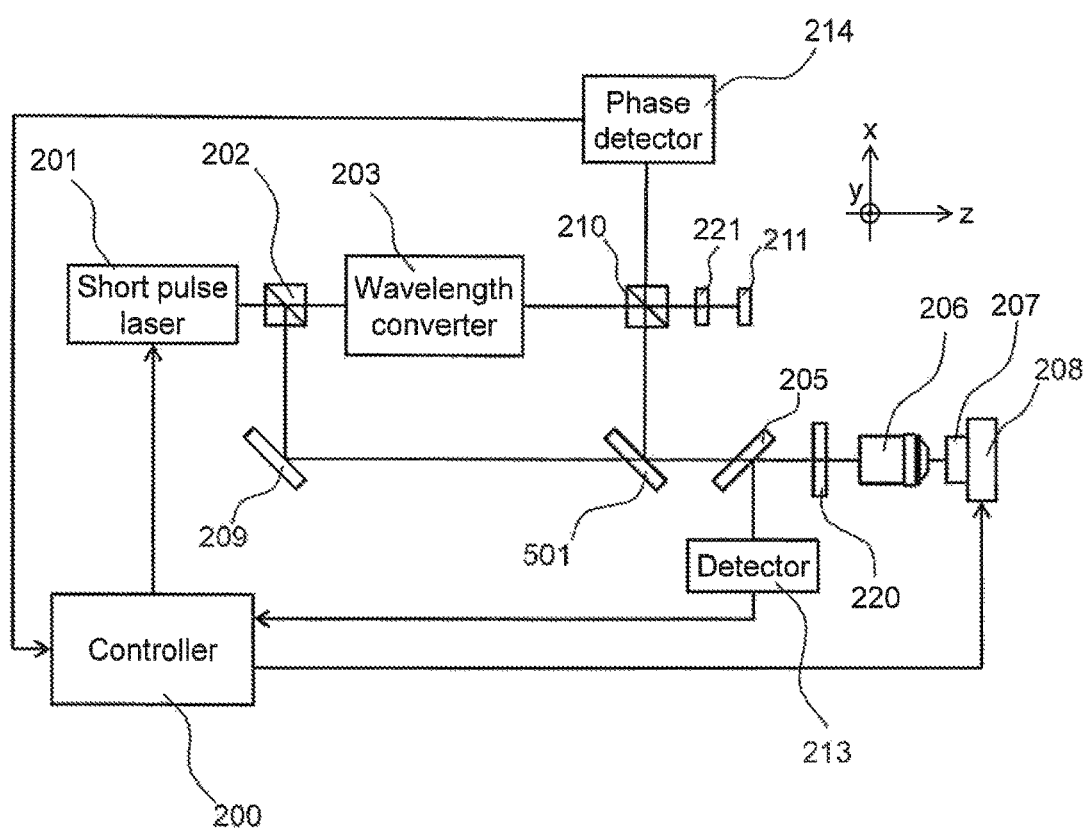
FIG. 5 is a schematic diagram when a Stokes beam is used for a phase sensor.

The position at which the phase sensor is disposed is not limited to those shown in FIGS. 1, 3, and 4. The phase sensor may be disposed at any position on the optical path of the pump beam, or may also be disposed on the optical path of the Stokes beam as shown in FIG. 5 if an OPO is used as the wavelength converter 203. It should be noted that a dichroic mirror 501 should reflect the Stokes beam and pass the pump beam. Thus, in this case, it is necessary to switch, in accordance with the wavelength sweep of the Stokes beam, the dichroic mirror to the one corresponding to the wavelength. For example, the dichroic mirror may be switched each time the wavelength of the Stokes beam is changed by 50 nm.

Figure 6:
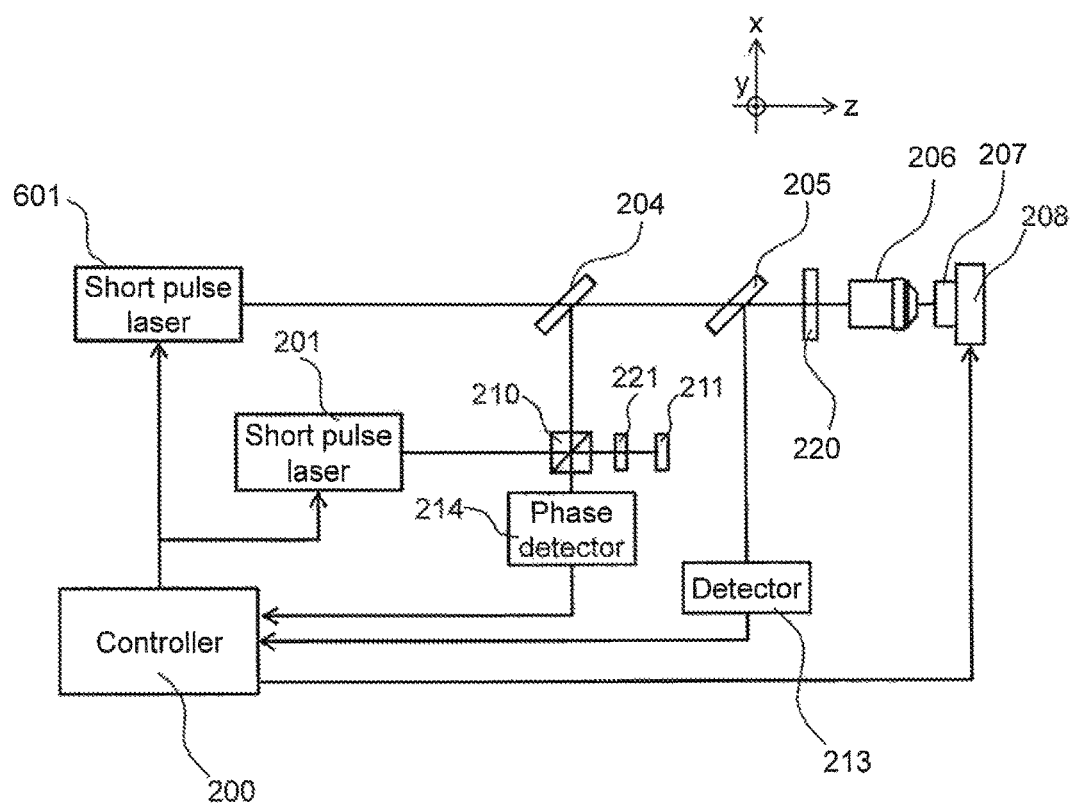
FIG. 6 is a schematic diagram of a device with two short-pulse laser sources.

The number of the short-pulse lasers used may be more than one. As shown in FIG. 6, a short-pulse laser source 601 may also be provided as a light source of the Stokes beam. In such a case, the short-pulse laser source 601 emits a laser beam in synchronism with the short-pulse laser source 201 under the control of the controller 200. As an example of the short-pulse laser source 601, a laser source with a broader spectrum than that of the short-pulse laser source 201, such as a femtosecond laser or a white laser with a photonic crystal fiber, is desirably used. However, it is also possible to use an OPO that is integrated with an excitation light source so that the wavelength is swept. The configuration in which two short-pulse laser sources are used is particularly advantageous when the power of the short-pulse laser source 201 is insufficient and a Stokes beam and a pump beam cannot be generated with a single short-pulse laser source.
(Configuration of the Phase Detector)

Figure 7:
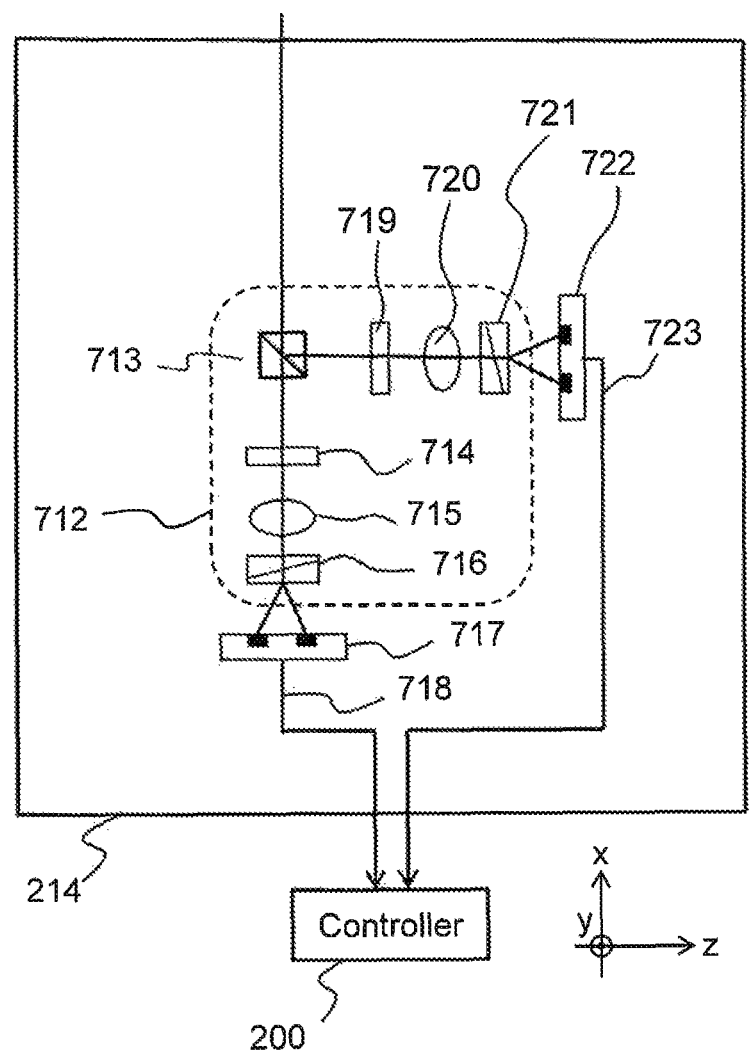
FIG. 7 is a configuration example of a phase detector of the phase sensor.

FIG. 7 is a configuration example of the phase detector 214. A combined beam of the signal beam and the reference beam obtained with the polarization beam splitter 210 becomes incident on interference optics 712 that include a half beam splitter 713, a λ/2 plate 714, a λ/4 plate 719, condensing lenses 715 and 720, and Wollaston prisms 716 and 721. The combined beam is split into a transmitted beam and a reflected beam by the half beam splitter 713. The transmitted beam passes through the λ/2 plate 714 whose optical axis is set at about 22.5 degrees with respect to the horizontal direction, and is then focused by the condensing lens 715 and is split by the Wollaston prism 716 so that a first interference beam and a second interference beam having a phase difference of 180 degrees are generated. The first interference beam and the second interference beam are detected by a current differential photodetector 717 so that a signal 718 that is proportional to the intensity difference between the two beams is output.

Meanwhile, the reflected beam from the half beam splitter 713 passes through the λ/4 plate 719 whose optical axis is set at about 45 degrees with respect to the horizontal direction, and is then focused by the condensing lens 720 and is split by the Wollaston prism 721, so that a third interference beam and a fourth interference beam having a phase difference of 180 degrees are generated. The third interference beam and the fourth interference beam are detected by a current differential photodetector 722 so that a signal 723 that is proportional to the intensity difference between the two beams is output. The thus generated signals 718 and 723 are input to the controller 200 and are operated, whereby a signal that is proportional to the intensity of the signal beam, and the phase of the signal beam with respect to the reference beam are obtained.
(Principle of the Phase Detector)

Hereinafter, the aforementioned operation principle will be described in detail using mathematical formulae. Provided that the Jones vector of the combined beam at a time point when it becomes incident on the interference optics 712 is represented as follows,

[Formula 1]

$$\begin{pmatrix} E_{sig} \\ E_{ref} \end{pmatrix}, \quad (1)$$

the Jones vector of the combined beam that has passed through the half beam splitter 713 and has further passed through the λ/2 plate 714 is represented as follows.

[Formula 2]

$$\begin{pmatrix} 1/\sqrt{2} & -1/\sqrt{2} \\ 1/\sqrt{2} & 1/\sqrt{2} \end{pmatrix} \begin{pmatrix} E_{sig}/\sqrt{2} \\ E_{ref}/\sqrt{2} \end{pmatrix} = \frac{1}{2} \begin{pmatrix} E_{sig} - E_{ref} \\ E_{sig} + E_{ref} \end{pmatrix} \quad (2)$$

The combined beam represented by Formula (2) is split into p-polarized components and s-polarized components by the Wollaston prism 716, which are then differentially detected by the current differential photodetector 717. Thus, the differential signal 718 is represented as follows.

[Formula 3]

$$I = \frac{1}{4}|E_{sig} + E_{ref}|^2 - \frac{1}{4}|E_{sig} - E_{ref}|^2 = |E_{sig}||E_{ref}|\cos(\theta_{sig} - \theta_{ref}) \quad (3)$$

Herein, symbols $\theta_{sig}$ and $\theta_{ref}$ are the phases when the complex numbers $E_{sig}$ and $E_{ref}$ are represented in polar coordinates, respectively. The conversion efficiency of the detector is set to 1 for the sake of simplicity.

Meanwhile, the Jones vector of the combined beam that has been reflected by the half beam splitter 713 and has further passed through the λ/4 plate 719 is represented as follows.

[Formula 4]

$$\begin{pmatrix} i/\sqrt{2} & 1/\sqrt{2} \\ 1/\sqrt{2} & i/\sqrt{2} \end{pmatrix} \begin{pmatrix} E_{sig}/\sqrt{2} \\ E_{ref}/\sqrt{2} \end{pmatrix} = \frac{1}{2} \begin{pmatrix} i(E_{sig} - iE_{ref}) \\ E_{sig} + iE_{ref} \end{pmatrix} \quad (4)$$

The combined beam represented by Formula (4) is split into p-polarized components and s-polarized components by the Wollaston prism 721, which are then differentially detected by the current differential photodetector 722. Thus, the differential signal 723 is represented as follows.

[Formula 5]

$$Q = \frac{1}{4}|E_{sig} + iE_{ref}|^2 - \frac{1}{4}|E_{sig} - iE_{ref}|^2 = |E_{sig}||E_{ref}|\sin(\theta_{sig} - \theta_{ref}) \quad (5)$$

These outputs are operated as follows by the signal processor of the controller 200, so that the phase of the signal beam with respect to the reference beam is obtained.

[Formula 6]

$$\theta_{sig} - \theta_{ref} = \arctan Q/I \quad (6)$$

In addition, a signal proportional to the intensity of the signal beam is obtained through the following operation. This means that the signal beam is amplified by the reference beam. Thus, a signal with a high S/N ratio is obtained.

[Formula 7]

$$|E_{sig}||E_{ref}| = \sqrt{I^2 + Q^2} \quad (7)$$

As described above, generating and detecting four interference beams having a phase difference of 90 degrees with respect to each other using the interference optics 712 can obtain a phase and an intensity signal. However, in principle, similar signals can be obtained with any number of interference beams as long as it is greater than or equal to three. For example, generating and detecting three interference beams having a phase difference of 120 degrees with respect to each other can obtain the same signals as those represented by Formula (6) and (7).

(Comparison with the Conventional OCT)

FIG. 8 is shows comparison between the phase sensor in accordance with the present scheme and the conventional OCT. The conventional OCT is broadly divided into the time domain OCT and the Fourier domain OCT depending on the scanning method. The Fourier domain OCT is further divided into spectral domain OCT and wavelength-scanning OCT depending on the light source. The time domain OCT is a scheme in which when the optical path length of a reference beam is changed by moving a mirror for the reference beam, an interference signal is obtained only when the optical path length of the reference beam coincides with that of a signal beam. The depth resolution of this scheme directly reflects the coherence length of the light source, and is about 10 μm.

The Fourier domain OCT is a scheme in which when the wavelength (wave number) of a light source is continuously changed, the frequency of a change in the intensity of an interference signal in the wave number space depends on the difference in optical path length between a reference beam and a signal beam. The wavelength-scanning OCT and the spectral domain OCT differ in that the wavelength-scanning OCT actually scans the wavelength, while the spectral domain OCT uses the spectral width of a low-coherence light source and a spectrometer. However, the essential principles of the two schemes are the same. The resolution of the Fourier domain OCT is determined by the spectral width of a light source and the measurement wavelength range of a spectrometer. For example, Opt. Express., Vol. 12, 367-376 (2004) describes a spectral domain OCT device with a resolution of 6 μm.

Meanwhile, the phase sensor in accordance with the present invention uses a scheme of focusing light beams through an objective lens with a high numerical aperture using a light source with a coherence length of greater than or equal to hundreds of pin. Unlike in the conventional OCT, the resolution depends not on the light source but on the numerical aperture of the objective lens. For example, using an objective lens with a numerical aperture of greater than or equal to 0.4 can surely obtain a depth resolution of less than or equal to 3 μm. FIG. 9 is a diagram showing the signal intensity obtained from an interface between glass and air using the phase sensor of the present invention (which has an objective lens with a numerical aperture of 0.5), where a resolution of 2.6 μm is achieved. Further, when not the intensity but the phase is detected, a resolution of less than or equal to 50 nm can be achieved.

The thickness of a cell membrane is less than or equal to 10 nm. With the conventional multi-modal measurement device that combines CARS and OCT, it has been impossible to acquire the molecular state on the surface of the cell membrane. However, with the configuration of the present invention, it is possible to detect the surface position of a cell membrane with high accuracy using the phase sensor, and obtain molecular information at the surface position at a high S/N ratio using reflective CARS that has a characteristic that the signal intensity increases on the surface.

(Principle of the Follow-Up Operation of the Phase Sensor)

Figure 10:
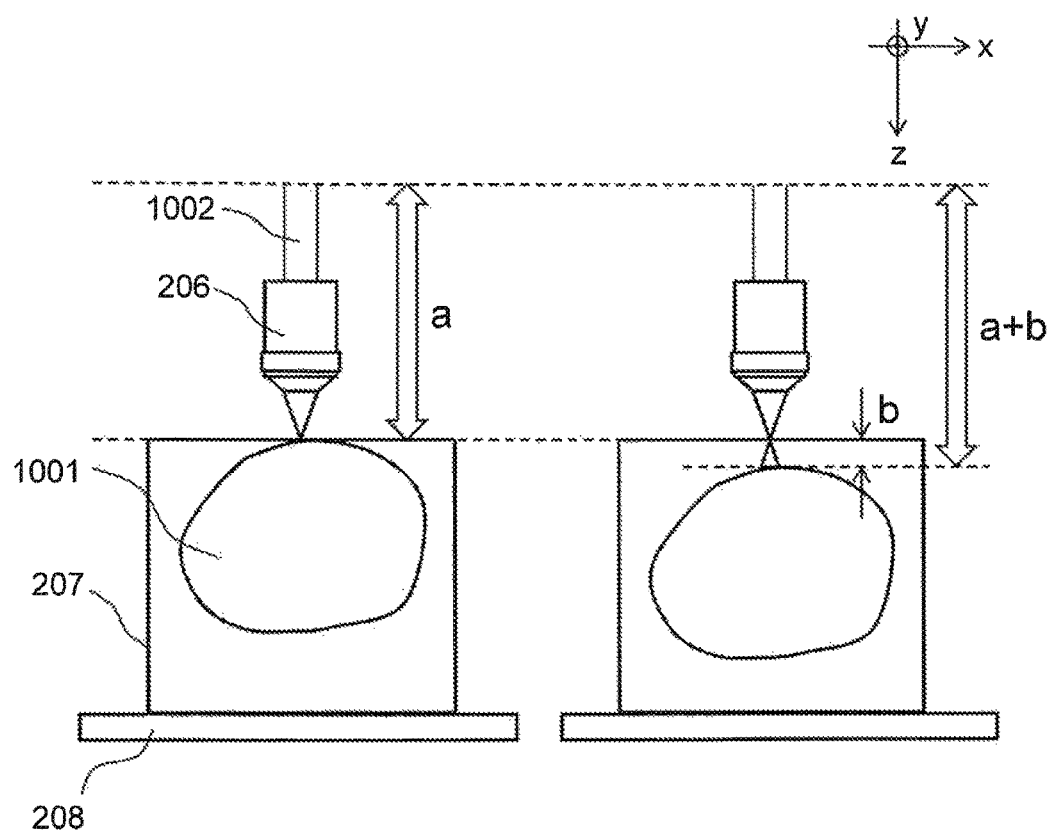
FIG. 10 is a diagram showing the principle of following the surface of a cell.
Figure 11:
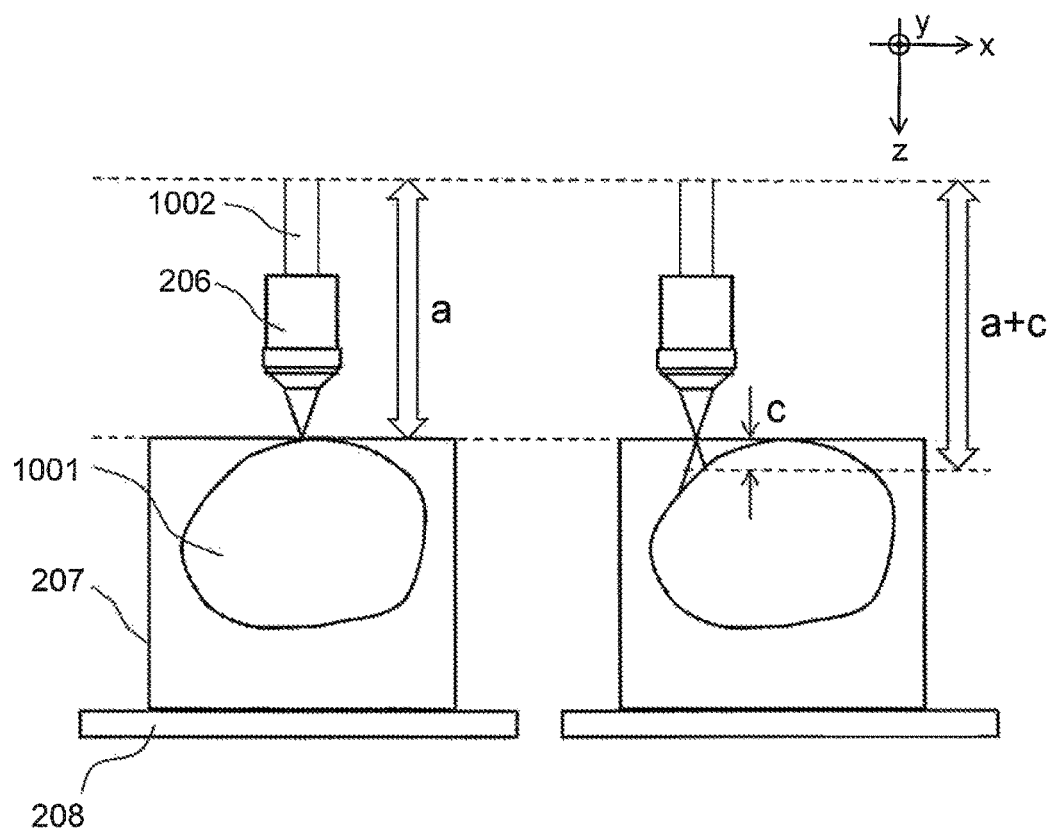
FIG. 11 is a diagram showing the principle of scanning a cell in the xy direction while following the surface of the cell.

FIGS. 10 and 11 each show the principle of the operation of following a surface with the phase sensor. It should be noted that herein, the relationship in size between a cell, an objective lens, and the like is displayed differently from the actual relationship for the sake of simplicity.

FIG. 10 is a diagram showing the principle of following the surface of a cell 1001 in the sample 207. When the position of the cell 1001 has changed by b in the z direction during observation, the optical path length changes from a to a+b. Thus, the phase and the intensity of the signal beam 1002, which is a reflected beam, change. When the sample stage 2008 is moved so as to compensate for such changes in the phase and the intensity, it becomes possible to follow the surface position of the cell 1001.

FIG. 11 is a diagram showing the principle of scanning the cell 1001 in the xy direction while following the surface of the cell 1001. When the sample stage 208 is moved in the xy direction, the phase and the intensity of the signal beam 1002 change in accordance with the shape of the cell 1001. When the stage 208 is moved so as to compensate for such changes, it becomes possible to follow the surface position while scanning the cell 1001 in the xy direction.

Although an example in which the sample 207 is moved by the sample stage 208 is shown herein, it is also possible to move the objective lens 206 with the configuration of FIG. 3. In such a case, the phase changes with a movement of the objective lens. Thus, the position of the objective lens in the z direction may be adjusted so that the intensity is within a predetermined range.

(Operation Flowchart)

Figure 12:
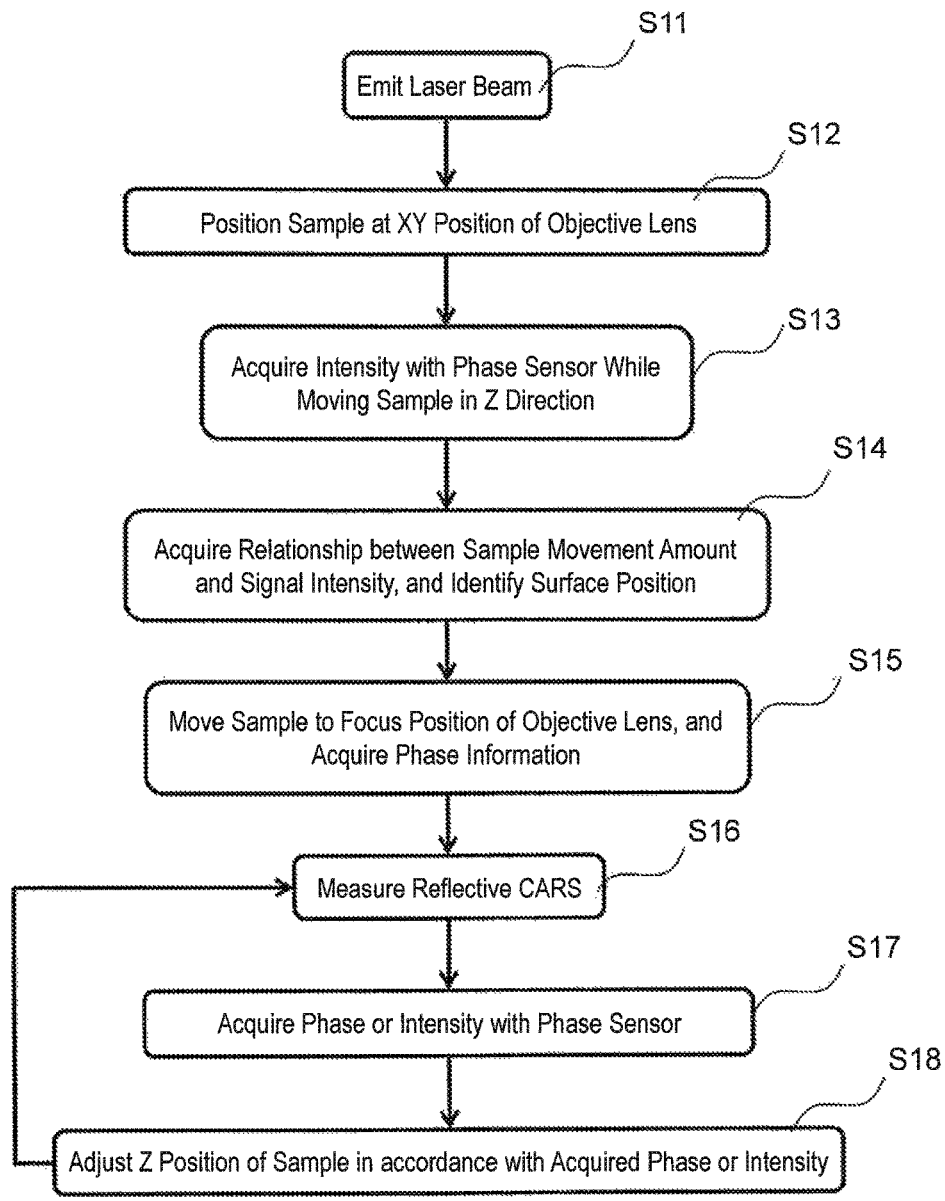
FIG. 12 is a flowchart showing an operation example of the device in accordance with the present invention.

FIG. 12 shows an example of an operation flowchart of up to the acquisition of molecular information by detecting the surface position of a cell or the like with the device in accordance with the present invention. Hereinafter, an example in which CARS is measured at a single point on the surface will be described.

In step 11, the short-pulse laser source 201 controlled by the controller 200 emits a laser beam. In step 12, a sample is positioned at the xy position of the objective lens. In step 13, the intensity information on the signal beam is acquired with the phase sensor while the sample is moved in the z direction. In step 14, the relationship between the sample movement amount and the signal intensity is acquired from the results in step 13 so that the surface position is identified. For identifying the surface position, a peak of the signal beam corresponding to the surface may be detected with the phase sensor, for example, and the position with the maximum intensity may be determined to be the surface. In step 15, the sample position is controlled so that a laser beam is focused onto the identified surface position, and the phase information on the signal beam is acquired from the surface.

In step 16, reflective CARS is measured, and the spectrum of the obtained CARS beam is analyzed to acquire molecular information. In step 17, the phase or the intensity is checked with the phase sensor, and if there is any change in the phase or the intensity from that acquired in step 15 or step 14, the sample position is adjusted in step S18 so as to compensate for such change. If the phase information acquired with the phase sensor is used for the adjustment of the sample position, the z position of the sample is adjusted in step 18 so that the phase acquired in step 17 becomes equal to that acquired in step 15. If the intensity information on the signal beam is used for the adjustment of the sample position, the z position of the sample is adjusted so that the intensity of the signal beam becomes maximum. Repeating the operations of from steps 16 to 18 can acquire molecular information by following the desired surface position even when the position of the cell in the sample has changed. In particular, when the surface is followed using the phase information, the position accuracy may improve by one digit or more as compared to when the intensity information is used. It should be noted that when a change in the position of the cell is small relative to the required measurement accuracy, the operations in steps 17 and 18 may be omitted.

Figure 13:
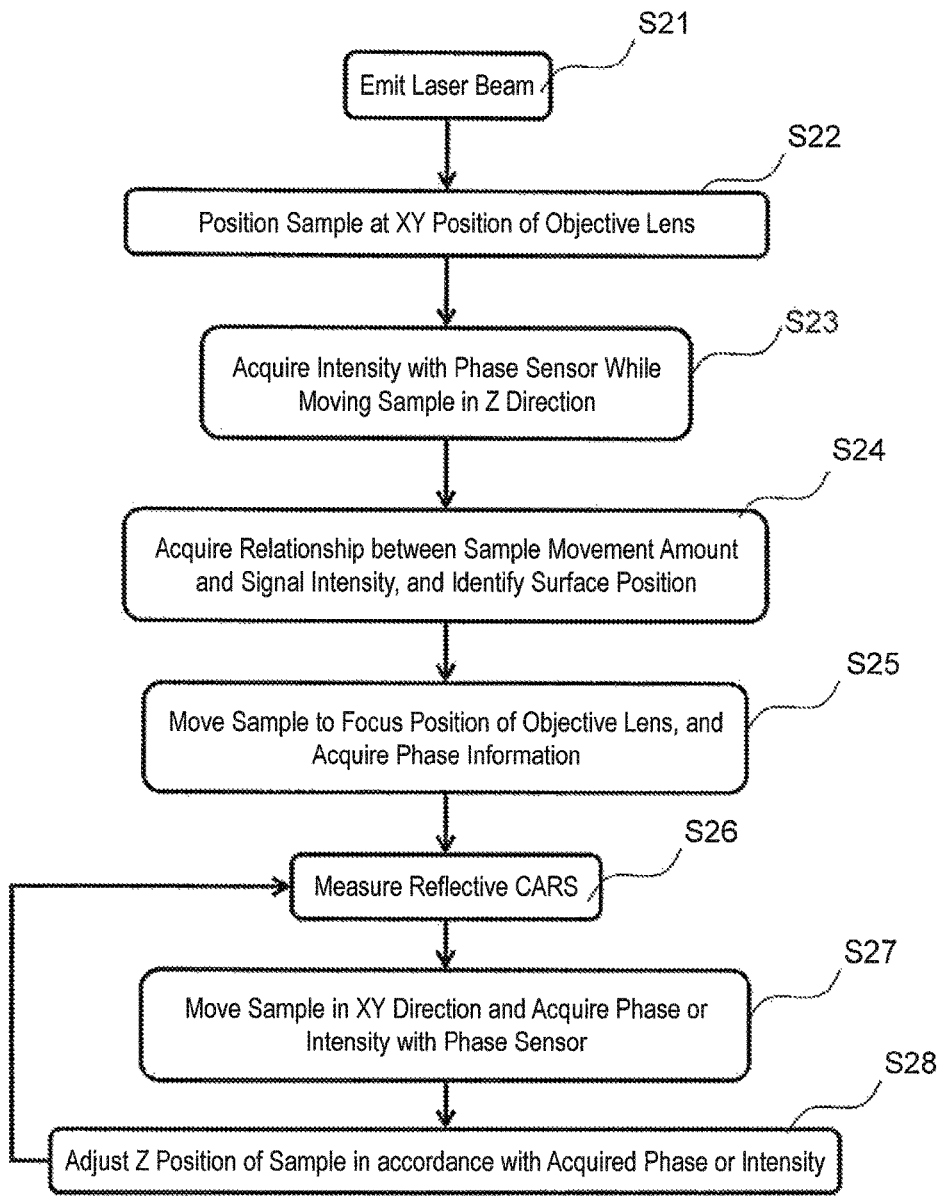
FIG. 13 is a flowchart showing an operation example in which a cell is scanned in the xy direction while the surface of the cell is followed.
Figure 14:
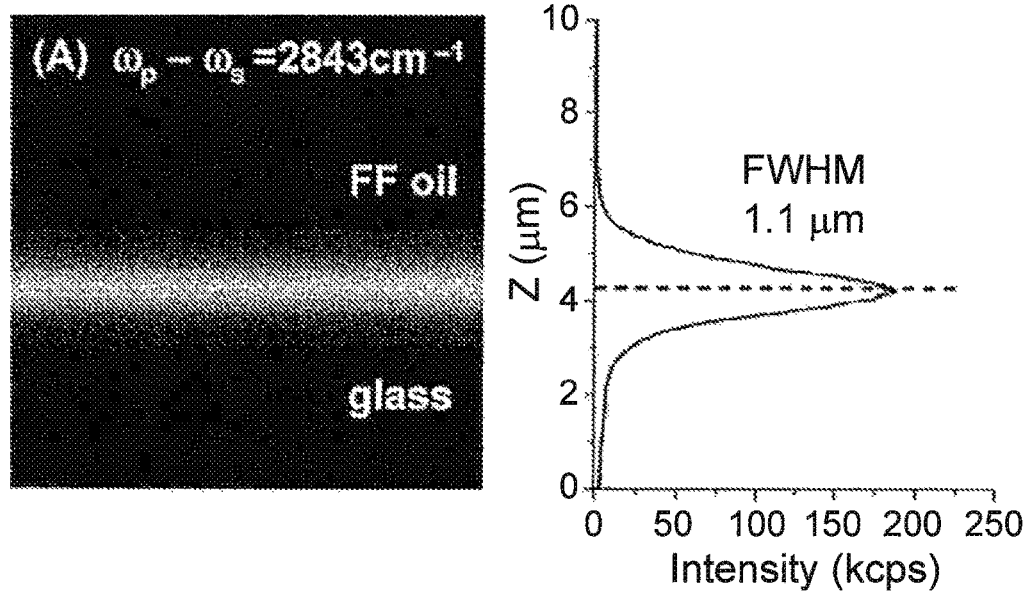
FIG. 14 is a diagram showing that a peak of a reflective CARS signal is obtained at an interface between oil and glass described in Non Patent Literature 1.

FIG. 13 is a flowchart showing an operation example in which a cell is scanned in the xy direction while the surface of the cell is followed. Steps 21 to 26 and step 28 correspond to steps 11 to 16 and step 18 in FIG. 12, and the operation performed in each step is the same as that in FIG. 12. In the flowchart shown in FIG. 13, the sample is moved in the xy direction in step 27 so that the phase or the intensity is acquired with the phase sensor, and in step 28, the z position of the sample is adjusted so that the phase or the intensity becomes equal to that acquired in step 25 or 24, whereby it becomes possible to measure CARS at each point on the surface and acquire a molecular distribution on the surface.

Although FIGS. 12 and 13 illustrate operation examples based on the configuration in which the stage of the sample shown in FIG. 1 is moved, it is also possible to move the objective lens with the configuration of FIG. 3. In such a case, the follow-up operation may be performed using not the phase but the signal intensity detected with the phase sensor.

It should be noted that the present invention is not limited to the aforementioned embodiments, and includes a variety of variations. For example, although the aforementioned embodiments have been described in detail to clearly illustrate the present invention, the present invention need not include all of the configurations described in the embodiments. It is possible to replace a part of a configuration of an embodiment with a configuration of another embodiment. In addition, it is also possible to add, to a configuration of an embodiment, a configuration of another embodiment. Further, it is also possible to, for a part of a configuration of each embodiment, add, remove, or substitute a configuration of another embodiment.

REFERENCE SIGNS LIST

200 Controller
201 Short-pulse laser source
202 Beam splitter
203 Wavelength converter
204 Dichroic mirror
205 Long-pass filter
206 Objective lens
207 Sample
208 Sample stage
209 Mirror
210 Polarization beam splitter
211 Mirror
213 Photodetector
214 Phase detector
220 $\lambda/4$ plate
221 $\lambda/4$ plate
225 Actuator
401 Optical path changing means
501 Dichroic mirror
601 Short-pulse laser source
712 Interference optics
713 Half beam splitter
714 $\lambda/2$ plate
715 Condensing lens
716 Wollaston prism
717 Photodetector
718 Differential signal
719 $\lambda/4$ plate
720 Condensing lens
721 Wollaston prism
722 Photodetector
723 Differential signal
1001 Cell
1002 Signal beam

The invention claimed is:

1. An optical measuring device comprising:
a sample stage that holds a sample;
a controller configured to control the optical measuring device;
a laser source configured to emit a laser beam;
a beam splitter configured to split the laser into a pump beam and a beam to be generated to a Stokes beam, the Stokes beam having a wavelength longer than that of the pump beam;
a polarization beam splitter configured to receive the pump beam and to split the pump beam into first polarized components and second polarized components, the second polarized components being a reference beam;
a dichroic mirror configured to reflect the first polarized components of the pump beam to coaxially combine the first polarized components of the pump beam with the Stokes beam into a combined beam;
an objective lens configured to focus the combined beam onto the sample held on the sample stage;
the controller is configured to control a relative position between the objective lens and the sample held on the sample stage;
a phase sensor configured to identify a surface position of the sample by causing a reflected beam from the sample that has passed through the objective lens and the reference beam to interfere with each other and detect an intensity of the reflected beam and/or a phase of the reflected beam with respect to the reference beam; and
a detector configured to detect a reflected CARS beam generated from the sample.

2. The optical measuring device according to claim 1, wherein the phase sensor is configured to detect the surface position of the sample with an accuracy of less than or equal to 3 micrometers in an optical-axis direction.

3. The optical measuring device according to claim 1, wherein a numerical aperture of the objective lens is greater than or equal to 0.4.

4. The optical measuring device according to claim 1, wherein the phase sensor includes an interferometer and the phase sensor is configured to output a signal proportional to the intensity of the reflected beam and a signal representing the phase of the reflected beam with respect to the reference beam.

5. The optical measuring device according to claim 1, further comprises a wavelength converter configured to generate the Stokes beam by converting a wavelength of a light beam emitted from the short-pulse laser source, and the Stokes beam being a wavelength longer than that of the pump beam.

6. The optical measuring device according to claim 1, wherein
the reference beam is split off from the pump beam, and
the phase sensor is configured to output a signal proportional to an intensity of the pump beam reflected from the sample and output a signal representing a phase of the pump beam reflected from the sample with respect to the reference beam.

7. An optical measuring method comprising:
splitting a pump beam into first polarized components and second polarized components, the second polarized components being a reference beam;
combining the first polarized components of the pump beam with a Stokes beam into a combined beam, the Stokes beam having a wavelength longer than that of the pump beam;

focusing the combined beam with an objective lens onto a sample;

irradiating the sample with the combined beam via the objective lens;

detecting a surface position of the sample with a phase sensor using an interference beam of a beam reflected from the sample and the reference beam that has not irradiated the sample;

adjusting a focus position of the objective lens to the detected surface position of the sample; and detecting a reflected CARS beam generated from the sample.

8. The optical measuring method according to claim 7, wherein the phase sensor is configured to detect the surface position of the sample using an intensity signal that is proportional to an intensity of the reflected beam and determine a phase of the reflected beam with respect to the reference beam upon detection of the surface position of the sample.

9. The optical measuring method according to claim 8, further comprising controlling a relative position between the objective lens and the sample in an optical-axis direction so that the determined phase is maintained.

* * * * *